(12) United States Patent
Chan et al.

(10) Patent No.: US 7,943,568 B2
(45) Date of Patent: May 17, 2011

(54) ANTITUMOR AGENTS

(75) Inventors: Kenneth K. Chan, Dublin, OH (US); Jin Xiao, Newbury Park, CA (US)

(73) Assignee: The Ohio State University Research Foundation, Columbus, OH (US)

( * ) Notice: Subject to any disclaimer, the term of this patent is extended or adjusted under 35 U.S.C. 154(b) by 297 days.

(21) Appl. No.: 12/088,846

(22) PCT Filed: Sep. 30, 2005

(86) PCT No.: PCT/US2005/035179
§ 371 (c)(1),
(2), (4) Date: Sep. 12, 2008

(87) PCT Pub. No.: WO2007/040522
PCT Pub. Date: Apr. 12, 2007

(65) Prior Publication Data
US 2009/0221473 A1    Sep. 3, 2009

(51) Int. Cl.
*A61K 38/00* (2006.01)
*C12N 5/00* (2006.01)
(52) U.S. Cl. .......................... 514/1.1; 435/375
(58) Field of Classification Search .................. None
See application file for complete search history.

(56) References Cited

U.S. PATENT DOCUMENTS

| | | | | |
|---|---|---|---|---|
| 6,670,326 B1 * | 12/2003 | Nagai et al. | .................. | 514/19.3 |
| 7,098,186 B2 * | 8/2006 | Nagai et al. | .................. | 514/19.3 |
| 7,314,862 B2 * | 1/2008 | Naoe et al. | .................... | 514/19.4 |

OTHER PUBLICATIONS

Nishino et al. Cyclic Tetrapeptides Bearing a Sulfhydryl Group Potently Inhibit Histone Deacetylases. Organic Letters. 2003. vol. 5, No. 26, pp. 5079-5082.*
Somech et al. Histone deacetylase inhibitors—a new tool to treat cancer. Cancer Treatment Reviews. 2004, vol. 30, pp. 461-472.*
Furumai et al. FK228 (Depsipeptide) as a Natural Prodrug That Inhibits Class I Histone Deacetylases. Cancer Res. 2002, vol. 62, pp. 4916-4921.*

* cited by examiner

*Primary Examiner* — Marcela M Cordero Garcia
(74) *Attorney, Agent, or Firm* — Calfee, Halter & Griswold LLP

(57) ABSTRACT

Compounds and methods useful for the treatment of cancer in subjects in need of such treatment. The compounds are metabolites of the compound FK228 which have been identified as possessing HDAC inhibitory activity and anticancer properties. Further provided are compounds and methods for inducing apoptosis in cancer cells. Further provided are compounds and methods for inhibiting HDAC in cancer cells.

26 Claims, 3 Drawing Sheets rat blood incubation, plasma rat blood incubation, rbc homogenate 1

ANTITUMOR AGENTS

STATEMENT ON FEDERALLY FUNDED RESEARCH

This invention was funded, at least in part, by National Institutes of Health Grant 1R21CA96323, the Federal government may have certain rights in this invention.

BACKGROUND OF THE INVENTION

Abnormal signal transduction pathways are well-recognized targets for anticancer chemotherapy. For the purpose of cancer intervention, two signal transduction pathways have drawn enormous attention as potential targets for anticancer chemotherapy.

The Receptor Tyrosine Kinase (RTK)→Ras→Raf-1→MEK→ERK signal transduction pathway has been intensively studied. It was one of the earliest and best elucidated pathways, and its deregulation is frequently associated with human cancers. The first level targets are RTKs. For example, erbB2/HER-2 receptor is commonly over-expressed in human breast cancer and ovarian cancers. As important is epidermal growth factor receptor (EGFR) deregulation. Agents targeted to EGFR, HER-2, platelet-derived growth-factor receptor (PDGFR), vascular endothelial growth factor receptor (VEGFR) and also RTK-associated kinases such as Src are currently under pre-clinical development, in clinical trials and on the market.

Downstream of RTK is Ras, which has been found to mutate frequently in human cancers. Activating point mutations of small GTPase Ras are present in about 30% of all human tumors. Constitutively active Ras induces growth factor independent cell proliferation and cell survival. The oncogene nature of Ras was shown by malignant transformation of epithelial cells by mutant Ras (i.e., Harvey Ras). Several agents have been tested clinically to block Ras. Ras antisense oligonucleotides block Ras translation, while farnesyl transferase inhibitors (FTIs) prevent Ras from proper post-translation modification (i.e., prenylation) and activation.

Further downstream in the RTK→Ras→Raf-1→MEK→ERK signal transduction pathway is Raf-1. Efforts for blocking Raf-1 led to discovery of a small-molecule Raf-1 kinase inhibitor BAY 43-9006, which is now in a phase I clinical trial in patients with advanced solid tumors. Raf-1 Antisense ISIS 5132 has entered phase II clinical trials in patients with advanced colon and lung cancers. A MEK inhibitor CI-1040 has shown promising preclinical pharmacologic results and has entered a phase I clinical trial for safety evaluation. Mitogen-activated protein kinases (MAPKs) are over-expressed in certain cancers such as human head and neck squamous cell carcinomas. This led to targeting MAPKs, such as ERK, c-Jun N-terminal kinase (JNK) and p38 for anticancer therapy. One example is ERK inhibitor PD98059, which has shown synergism with docetaxel in inducing apoptosis of androgen-independent human prostate cancer cells. JNK inhibitor SP600125 and JNK antisense molecules reduce proliferation of all breast cancer cell lines. Moreover, inhibitors of p38 (i.e., PD169316, SB203580 and SB202190) can augment bisphosphonate (BPs)-induced growth inhibition of breast carcinoma.

The p53 tumor suppressor gene plays an indispensible role in two key processes: to induce cell cycle arrest at the G1/S transition along with DNA repair, or if DNA repair is impossible, to activate apoptosis. The p53 protein functions through transcriptional activation of various downstream effecter genes (i.e., CDK inhibitor p21$^{CIP1/WAF}$), which have promoters containing p53-specific binding sites. Mutation of p53 is observed in over half of all sporadic cancers, making p53 mutations the most common genetic change in human cancers. The first strategy in targeting p53 is via MDM2, an oncogene that antagonizes p53 function by either repressing transcription of p53 or by induction of ubiquitin-mediated proteolysis of p53. Peptide inhibitors and antisense oligonucleotides against MDM2 showed positive results in model cancer cells. Another strategy is to reactivate p53 in tumor cells. This includes gene delivery using adenovirus (ONYX-015), which can only replicate in mutant p53 cells. Small molecules that stabilize p53 (i.e., CP-31398) have also received clinical interest.

Apoptosis of cancer cells is induced by many chemotherapeutic agents. Progress in elucidation of apoptosis machinery and mechanism has provided numerous potential molecular targets for anticancer therapy. One important family of apoptosis proteins is the BCL2 family. BCL2, an oncoprotein, has become an important target for anticancer chemotherapy since BCL2 deregulation has been frequently associated with malignant transformation and acquisition of drug resistance. One approach to turn off BLC2 is by antisense oligonucleotides such as G3139, which is now under phase II/III clinical trials.

Some endogenous angiogenisis inhibitors (e.g., angiostatin and endostatin) have been used clinically against tumor angiogenisis and metastasis. Angiostatin is a proteolytic fragment of collagen type XVIII. Clinical studies showed positive results when they were used either alone or in combination with other chemotherapeutic agents.

Accordingly, a need exists for new chemotherapeutic agents which can induce apoptosis in cancer cells. New agents should be have toxicity that is highly selective towards cancer cells at nM levels as well as have potent antitumor activities.

SUMMARY OF THE INVENTION

Provided herein are compounds and methods for treating or preventing cancer in a subject in need of such treatment. The compounds are a set of metabolites of FK228 shown as compounds A, B, C, D, E, F:

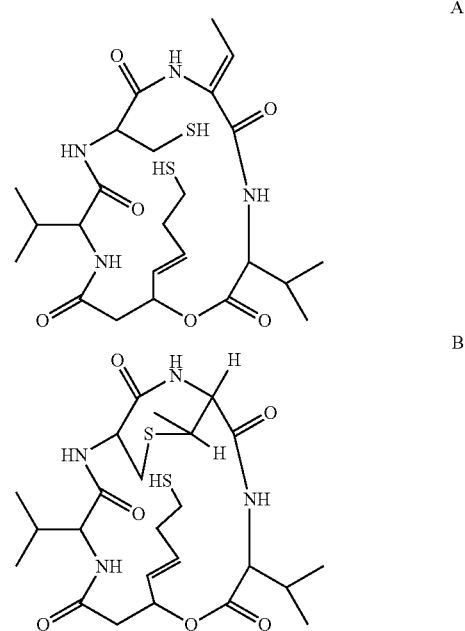

-continued

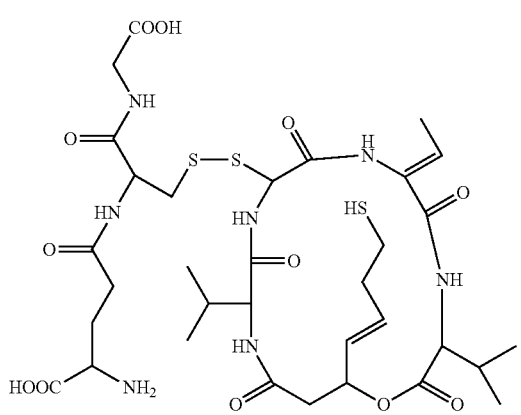
C

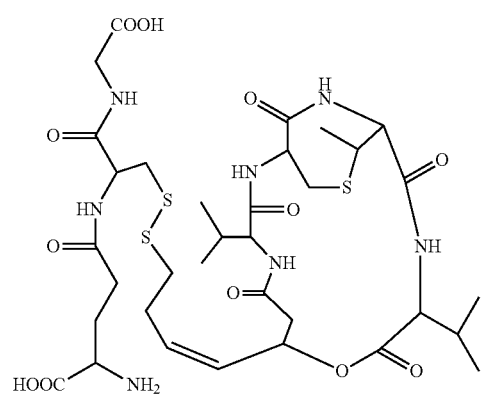
D

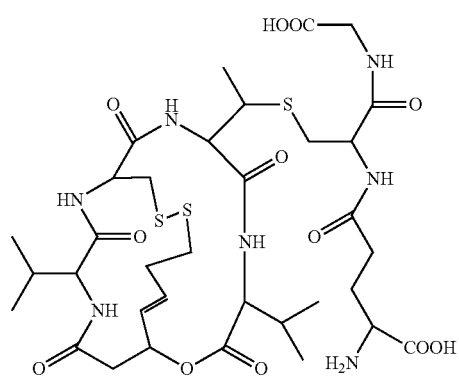
E

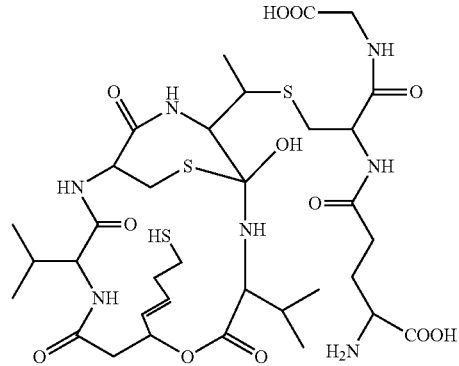
F

According to the methods provided herein, a therapeutically effective amount of one or more compounds of formulae A-F, and salts and derivatives thereof, is administered to a subject in need of such treatment. The compounds and methods described herein are useful in the treatment of leukemia, melanoma, colon cancer, sarcomas, lung cancer, stomach cancer, thyroid cancer, and lymphoma. Specifically, these compounds and methods are useful in the treatment of cancers including P338 leukemia, L1210 leukemia, B16 melanoma, Colon 38 carcinoma, M5076 reticulum cell sarcoma, Meth A fibrosarcoma, Lu-65 lung carcinomas, LC-6 lung carcinomas, SC-6 stomach adenocarcinoma, murine Meth A fibrosarcoma, human SC-6 stomach adenocarcinoma, thyroid cancer, actue myeloid leukemia, Chronic Lymphocytic Leukemia, cutaneous T cell lymphoma, peripheral T cell lymphoma, follicular lymphoma, non-Hodgkin's lymphoma, anaplastic large cell lymphoma, mycosis fungoides and Sezary syndrome.

Also provided are compounds and methods for inducing apoptosis in cancer cells; the method, contacting the cancer cells with a therapeutically effective amount of one or more metabolites of FK228:

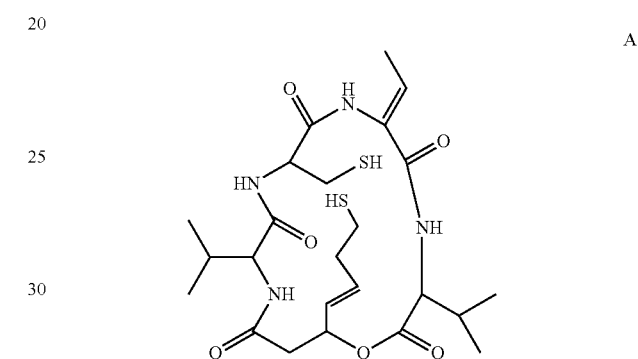
A

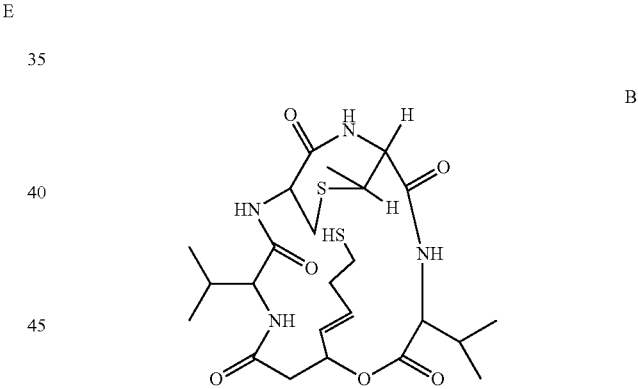
B

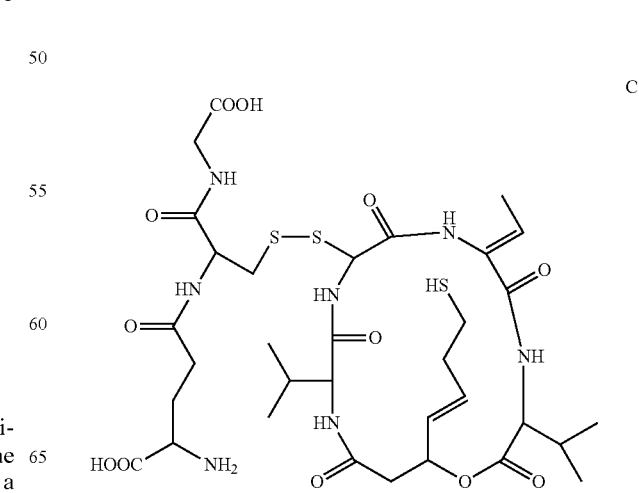
C

D
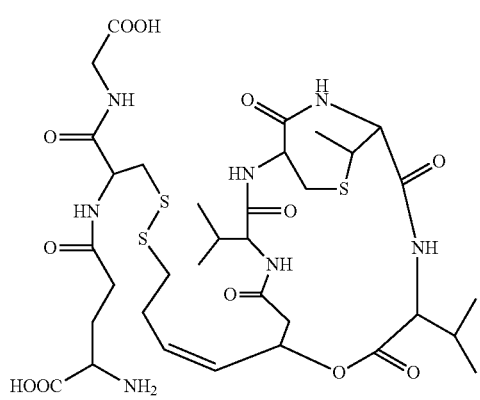
E
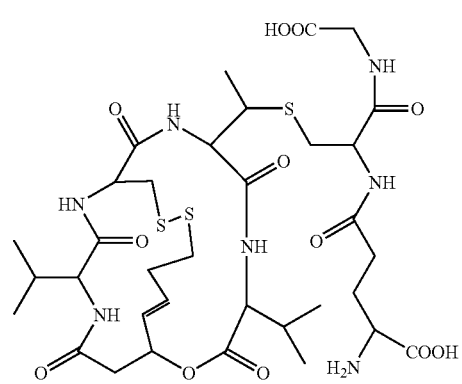
F
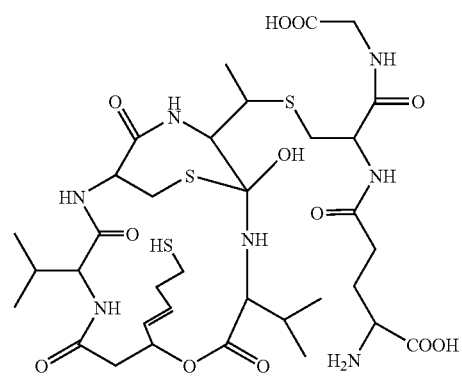
and salts and derivatives thereof.
Further provided is a method of inhibiting HDAC in cancer cells. According to the method provided herein, HDAC may be inhibited in cancer cells by contacting the cells with a biologically active amount of one or more metabolites of FK228, especially those of formulae A-F:
A
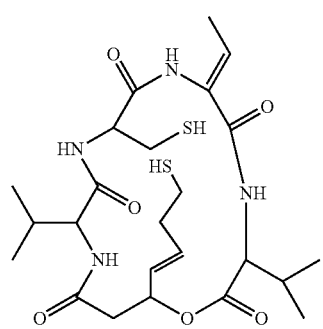
B
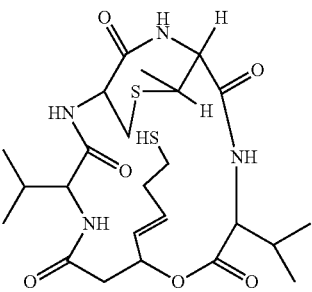
C
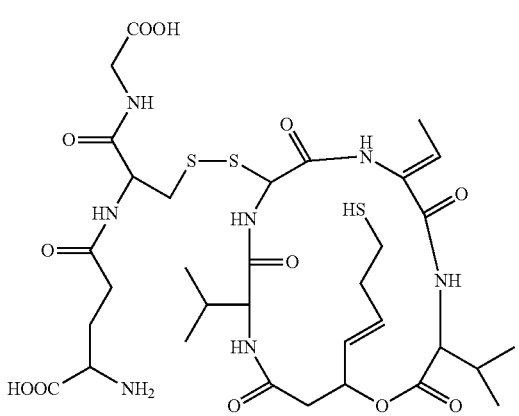
D
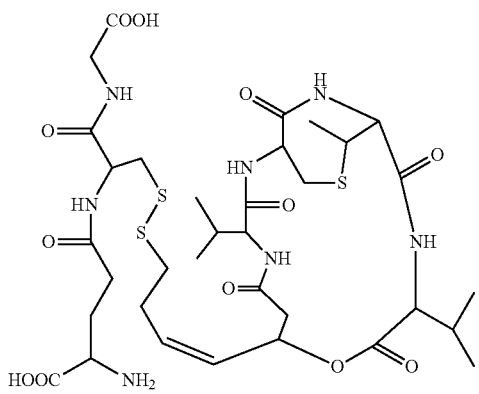
E
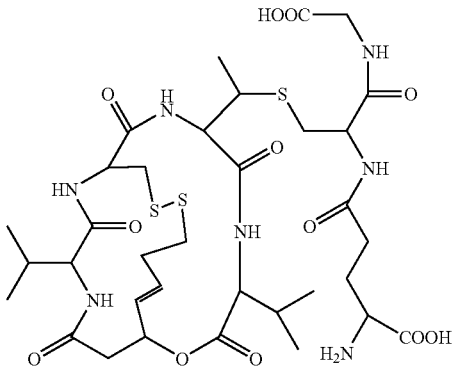

-continued

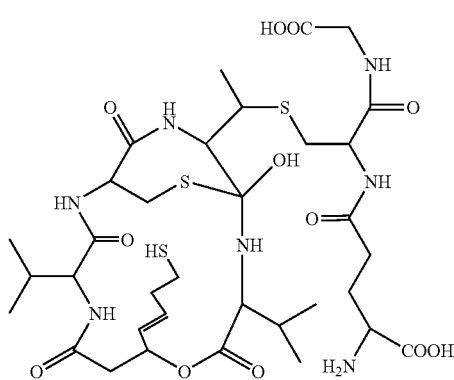
F

The method of inhibiting HDAC in cancer is useful for many types of cancer cells, including but not limited to leukemia, melanoma, colon cancer, sarcomas, lung cancer, stomach cancer, thyroid cancer, and lymphoma cells, and further including P338 leukemia, L1210 leukemia, B16 melanoma, Colon 38 carcinoma, M5076 reticulum cell sarcoma, Meth A fibrosarcoma, Lu-65 lung carcinomas, LC-6 lung carcinomas, SC-6 stomach adenocarcinoma, murine Meth A fibrosarcoma, human SC-6 stomach adenocarcinoma, thyroid cancer, actue myeloid leukemia, Chronic Lymphocytic Leukemia, cutaneous T cell lymphoma, peripheral T cell lymphoma, follicular lymphoma, non-Hodgkin's lymphoma, anaplastic large cell lymphoma, mycosis fungoides and Sezary syndrome.

DETAILED DESCRIPTION OF THE INVENTION

Figure 1:
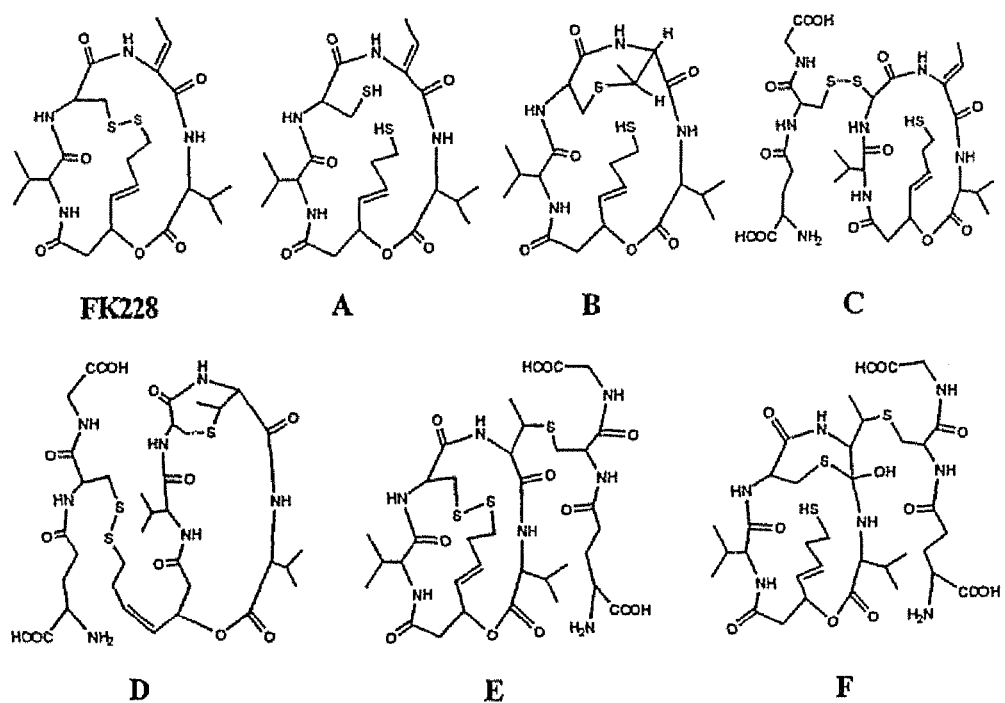
FIG. 1 shows the structures of FK228 and metabolites based on HPLC/MS$^n$ techniques.

Apoptosis represents programmed cell death that is important to maintain balance between normal and abnormal cell growth in a living system. Cancer cells manage to evade this process by mechanisms to maintain cell survival and abnormal cell growth. Many chemotherapeutic agents are designed to induce apoptosis of cancer cells. Progress in elucidation of apoptosis machinery and mechanism has provided numerous potential molecular targets for anticancer therapy. One important pathway is sending signals through cell surface receptors, particularly the mitogen pathway (Src) or growth factor (EGF/Erb) to inhibit the activation of Ras oncogenic proteins or the Ras/Raf pathway. Depsipeptide FK228 has been found to possess activity to reverse this pathway and down-regulate c-myc expression. We have found and characterized several metabolites of FK228 described herein and shown in FIG. 1. These agents are much more potent HDAC inhibitors than FK228, and much more potent anti-cancer agents than FK228. Furthermore, unlike FK228, these metabolites may be delivered specifically to target cells, thus making them more desirable agents for the treatment and prevention of diseases involving unwanted rapidly proliferating cells, such as cancers.

As used herein, "treating" means curing, ameliorating or tempering the severity of the cancer or the symptoms associated therewith. The terms "treating," "treatment," and "therapy" as used herein refer to curative therapy, prophylactic therapy, and preventative therapy.

"Preventing" or "prevention" means preventing the occurrence of the cancer, or tempering the severity of the cancer if it is develops subsequent to the administration of the instant compositions. This preventing the onset of a clinically evident unwanted cell proliferation altogether or preventing the onset of a preclinically evident stage of unwanted rapid cell proliferation in individuals at risk. Also intended to be encompassed by this definition is the prevention of metastatis of malignant cells or to arrest or reverse the progression of malignant cells. This includes prophylactic treatment of those at risk of developing precancers and cancers.

The terms "therapeutically effective" and "pharmacologically effective" are intended to qualify the amount of each agent which will achieve the goal of improvement in disease severity and the frequency of incidence over treatment of each agent by itself, while avoiding adverse side effects typically associated with alternative therapies.

The term "subject" for purposes of treatment includes any human or animal subject having a neoplasia, such as cancer or precancer. For methods of prevention the subject is any human or animal subject, and preferably is a human subject who is at risk of developing a cancer. The subject may be at risk due to exposure to carcinogenic agents, being genetically predisposed to disorders characterized by unwanted, rapid cell proliferation, and so on. Besides being useful for human treatment, the compounds of the present invention are also useful for veterinary treatment of mammals, including companion animals and farm animals, such as, but not limited to dogs, cats, horses, cows, sheep, and pigs. Preferably, subject means a human.

The agents of the present invention may be administered orally, intravenously, intranasally, rectally, or by any means which delivers an effective amount of the active agent to the tissue or site to be treated. It will be appreciated that different dosages may be required for treating different disorders. An effective amount of an agent is that amount which causes a statistically significant decrease in neoplastic cell count, growth, or size. Neoplastic disorders responsive to the agents of the present invention include, but are not limited to, breast cancer.

The dosage form and amount can be readily established by reference to known treatment or prophylactic regiments. The amount of therapeutically active compound that is administered and the dosage regimen for treating a disease condition with the compounds and/or compositions of this invention depends on a variety of factors, including the age, weight, sex, and medical condition of the subject, the severity of the disease, the route and frequency of administration, the particular compound employed, the location of the unwanted proliferating cells, as well as the pharmacokinetic properties of the individual treated, and thus may vary widely. The dosage will generally be lower if the compounds are administered locally rather than systemically, and for prevention rather than for treatment. Such treatments may be administered as often as necessary and for the period of time judged necessary by the treating physician. One of skill in the art will appreciate that the dosage regime or therapeutically effective amount of the inhibitor to be administrated may need to be optimized for each individual. The pharmaceutical compositions may contain active ingredient in the range of about 0.1 to 2000 mg, preferably in the range of about 0.5 to 500 mg and most preferably between about 1 and 200 mg. A daily dose of about 0.01 to 100 mg/kg body weight, preferably between about 0.1 and about 50 mg/kg body weight, may be appropriate. The daily dose can be administered in one to four doses per day.

The active agents may be administered along with a pharmaceutical carrier and/or diluent. The agents of the present invention may also be administered in combination with other agents, for example, in association with other chemotherapeutic or immunostimulating drugs or therapeutic agents. Examples of pharmaceutical carriers or diluents useful in the present invention include any physiological buffered medium, i.e., about pH 7.0 to 7.4 comprising a suitable water soluble organic carrier. Suitable water soluble organic carriers include, but are not limited to corn oil, dimethylsulfoxide, gelatin capsules, etc.

Also included in the family of heteroaryl-containing isoflavone compounds are the pharmaceutically acceptable salts thereof. The phrase "pharmaceutically acceptable salts" connotes salts commonly used to form alkali metal salts and to form addition salts of free acids or free bases. The nature of the salt is not critical, provided that it is pharmaceutically acceptable. Also included in the family of heteroaryl-containing isoflavone compounds are esters thereof. Esters of the heteroaryl-containing isoflavone compounds may be prepared by conventional methods known to those skilled in the art.

Suitable pharmaceutically acceptable acid addition salts of heteroaryl-containing isoflavone compounds may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic, and sulfonic classes of organic acids, examples of which include formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, ambonic, pamoic, methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, galactaric, and galacturonic acids.

Suitable pharmaceutically acceptable base addition salts of heteroaryl-containing isoflavone compounds include metallic salts made from aluminum, calcium, lithium, magnesium, potassium, sodium, and zinc. Alternatively, organic salts made from N,N'-dibenzylethylenediamine, chloroprocaine, choline, diethanolamine, ethylenediamine, meglumine (N-methylglucamine) and procaine may be used form base addition salts of the heteroaryl-containing isoflavone compounds. All of these salts may be prepared by conventional means from the corresponding heteroaryl-containing isoflavone compounds by reacting, for example, the appropriate acid or base with the heteroaryl-containing isoflavone compounds.

The phrase "adjunct therapy" (or "combination therapy"), in defining use of a compound of the present invention and one or more other pharmaceutical agent, is intended to embrace administration of each agent in a sequential manner in a regimen that will provide beneficial effects of the drug combination, and is intended as well to embrace co-administration of these agents in a substantially simultaneous manner, such as in a single formulation having a fixed ratio of these active agents, or in multiple, separate formulations for each agent.

There are large numbers of antineoplastic agents available in commercial use, in clinical evaluation and in pre-clinical development, which could be selected for treatment of cancers or other neoplasias by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents. Alternatively, other anti-neoplastic agents, such as metallomatrix proteases inhibitors may be used. Suitable agents which may be used in combination therapy will be recognized by those of skill in the art.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable carrier.

For intravenous, intramuscular, subcutaneous, or intraperitoneal administration, the compound may be combined with a sterile aqueous solution which is preferably isotonic with the blood of the recipient. Such formulations may be prepared by dissolving solid active ingredient in water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

It has been found that FK228 possesses signal transduction activity through Ras pathways. Additionally, we have found that FK228 induces $p21^{Cip1}$ expression independent of the p53 status, increases phophorylation of Bcl-2, and activation of a novel p33MBP kinase, all leading into apoptotic and possible antitumor effects. Although we originally looked at only FK228, herein we focus on FK228 metabolites, which we show are even more potent anticancer agents.

As our knowledge accumulates about tumorigenesis, it appears that epigenic deregulation plays as important a role as does the genetic abnormality. DNA methylation, its regulation, its regulation and how its deregulation is related to cancer has been reviewed recently (cite). DNA methylation is mediated by a family of enzymes called DNA methyltranferases. Some small molecule inhibitors (e.g., 5-azacytidine and 5-aza-2'-doxycytidine) that target DNA methyltransferases have demonstrated encouraging activity against leukemia but not solid tumors. The antisense drug MG98, which is directed against the 3' untranslated region of the DNA methyltransferase-1 enzyme MnRNA, is now under phase II study. Another emerging epigenetic target is a family of enzymes called deacetylases, which is discussed below.

Histone Deacetylase Inhibitors as Anticancer Drugs

Histone Acetyltransferases

The eukaryotic nucleosome consists of 146 base pairs of DNA wrapped on a histone octamer core, which are arranged as a (H3-H4)2 tetramer and two H2A-H2B dimers. Under physiological conditions, the lysines on histone proteins bear positive charges and bind to the negatively charged phosphates on the DNA backbone. It has been 40 years since it was proposed that transcriptional competence is governed by histone acetylation status, which is determined by two families of enzymes, histone acetyltransferases (HATs). HATs, once recruited by transcriptional factors bound to the target gene sequence, promote acetylation of the lysine groups on histone proteins. This interferes with folding of the histone N-terminal tails and destabilizes the electrostatic bonds between DNA phosphates and histone lysines, resulting in an open DNA conformation (euchromatin) for gene transcription. On the other hand, HDACs promote histone deacetylation (heterochromatin) and result in gene silencing.

HDACs are divided into 3 classes on the basis of their homology to yeast histone deacetylases as summarized in table 1.3. These HDACs differ in their gene coding sequences, intracellular localizations, substrate specificities and cofactor requirements. The structures of the Class I HDACs resemble RPD3, a yeast transcriptional regulator with HDAC activity. This class includes HDAC1, 2, 3 and 8. All four members of this class reside in the nucleus and are sensitive to most known HDAC inhibitors. Class II HDACs are yeast histone deactylase-A1 (Had-1)-like and include at least HDAC 4, 5, 6, 7, 9, 10 and 11. The Class II HDACs are able to shuttle in and our of the nucleus in response to certain cellular signals and are sensitive to HDAC inhibitors as well. Class III HDACs are silent information regulator 2 (SIR2)-like proteins and include at least 7 members (SIRT1 to SIRT7). In contrast to the other two classes, SIRTs are NAD+ dependent and are insensitive to HDAC inhibitors. HDACs play essential roles in embryo development. It has been estimated that depending on cell type, inhibition of HDACs in cancer cells can lead to transcriptional activation and silencing of about 2% of human genes.

Similar to HATs, HDACs do not bind to DNA sequences directly, bar are recruited as a complex with other transcription co-repressors. Different HDACs may form many different complexes. The best-characterized HDAC complex involves Rpd3-like Class I HDACs (i.e., HDAC 1 and 2). First, certain sequence-specific tranceriptional repressors, such as the Mad-Max heterodimer, unligated retinoic acid receptor α-retinoid-X receptor heterodimer (RARα-RXR), and thyroid receptor (TR), bind to their target DNA promoter sequence. These repressors then exert their silencing function by recruiting the HDAC complex. The complex that contains HDAC1 or HDAC2 in association with the co-repressors Sin3A/B may further interact with nuclear co-repressor (N-CoR) and the silencing mediator or retinoic acid and thyroid hormone receptor (SMRT). N-CoR and SMRT are two silencing mediators for unliganded retinoid and thyroid hormone receptors. Moreover, a synergism of histone deacetylation and DNA methylation in tranicriptional repression is achieved by interaction of the HDAC complex with sequence non-specific repressor methyl-CpG-binding protein 2 (MeCP-2).

The activity of HDACs is subject to post-translational modification. Phosphorylation of HDACs leads to increased deacetylation of HDACs including at least HDAC1. On the other hand, the specificity of HDACs may be altered upon phosphorylation as suggested by studies of yeast histone deacetylase HD1.

HDACs are not only responsible for epigenetic modulation by deacetylating histone proteins, but are also involved in post-translational modification of non-histone proteins. For example, it has been reported that p53 exists in both the active acetylated form and the inactive deacetylated forms. Acetylated p53 shows dramatically higher binding affinity to its target sequence than does the unmodified form. The deactylation of p53 is mediated by HDACs.

Histone acetylation occurs at the $\epsilon$ amino groups of evolutionarily conserved lysine residues at the N-termini. All core histones can be acetylated in vivo. However, modifications of histones H3 and H are much more extensively characterized than those of H2A and H2B. Important positions for acetylation of Lys9 and Lys14 on histone H3 and, and Lys5, Lys8, Lys12, and Lys16 on histone H. Approxiately 15% of the core histone proteins undergo rapid acetylation and deacetylation. Since both HATs and HDACs need to be recruited to their target histones by transcription factors and complexes, which are generally associated with responsive elements at target gene promoters, it is expected that histone proteins with rapid (de)acetylation dynamics are also in proximity to gene promoter regions.

It is important to realize that post-translational modification of chromatin histones involves not only (de)acetylation, but also methylation, phosphorylation, ubiquitylation, and ADP ribosylation.

Recent advances in cancer physiopathology indicate that tumorigenisis may be associated with repression of transcription through abnormal recruitment.

Recently, HDAC upregulation has been found in prostate cancer and breast cancer. This suggests that HDAC deregulation may be directly involved in tumorigenisis.

HDAC Inhibitors

Some representative HDAC inhibitors include butyric acid, MS-27-275, SAHA, Trichostatin A, apicidin, oxanflatin, FK228, and trapoxin. These inhibitors can be divided into several classes based on their structures, including short-chain fatty acids (butyrates and Valproic acid), hydroxamic acids (Trichostatin A and SAHA), cyclic tetrapeptides (depsipeptide), benzamides (MS-27-275), and epoxide-containing agents (trapoxin). Most of them inhibit HDACs in a reversible manner except trapoxin, which possesses an epoxide group capable of irreversibly alkylating HDACs. The reversible inhibitors generally have a long aliphatic tail containing a nucleophilic end, such as —SH or —OH, which interacts with the active zinc center located on the bottom of HDAC binding pocket. Other HDAC inhibitors are emerging based on modification of the listed structures. Most of the new agents are derivatives of hydroxamic acids, including amide analogues of Trichostatin A (TSA) and thio/phosphorus-based SAHA. Replacement of the amide linkage in MS-27-275 structure with a sulfonamide led to discovery of a new class of potent HDAC inhibitors. Promising HDAC inhibitors that have entered clinical trials include hydroxamic acid derivative LAQ824, butyric acid derivative Titan, valproic acid, MS-27-275, SAHA, and depsipeptide FK228.

HDAC inhibitors cause transcriptional activation or repression of target genes (i.e., upregulation of p21 and downregulation of c-Myc), cell cycle arrest, differentiation, and apoptosis in cancer cells. Detailed pharmacological properties of HDAC inhibitors are discussed in the following section with a novel HDAC inhibitor KF228 as an example. However, it is likely that different HDAC inhibitors have different pharmacological properties. This is suggested by differences in their inhibition mechanism and specificity. For example FK228 specifically inhibits Class I HDACs, while TSA and its derivatives inhibit both Class I and Class II HDACs. Moreover, some HDAC inhibitors may cause apoptosis in cancer cells by mechanisms that are not apparently linked to their HDAC inhibitory activity. As discussed below, the FK228 derivatives described herein may cause cancer cell apoptosis by its angiostatic and microtubule-disturbing properties, which have not been reported for other HDAC inhibitors. This suggests that HDAC inhibitors, although grouped as a single class of anticancer agents due to their HDAC inhibitory activity, may cause different pharmacological effects in cancer cells.

Depsipeptide FK228, a Novel HDAC Inhibitor

Chemistry Depsipeptide FK228 (FR901228, NSC630176) was first isolated from *Chromobacterium violaceum* by the Fujisawa Company during a screening for microbial metabolites that induce transcriptional activation of the SV40 promoter. Its composition is $C_{24}H_{36}N_4O_6S_2$ with molecular weigh 540. Its structure was elucidated to be (E)-(1S,4S,10S, 21R)-7-[(Z)-ethylidene]-4,21-diisopropyl-2-oxz-12,13-dithia-5,8,20,23-tetraazabicyclo[8,7,6]-tricos-16ene-3,6,9, 19,22-pentanone, a bicyclic tetra-peptide with a disulfide linkage. Since FK228 production in the bacteria is of trace amount, a fermentation method for production of highly pure FK228 was developed, and improved later. A total 1-step synthesis of FK228 has also been developed.

FK228 has a unique cyclic structure when compared with other HDAC inhibitors. It is the only one that does not possess a tail-like aliphatic chain and a nucleophilic functional group that are thought to be required to block the active binding pocket of HDAC proteins. This raises the question whether FK228 blocks HDACs by the same mechanism as other reversible HDAC inhibitors, since it seems impossible for its bulky structure to fit in the narrow HDAC binding pocket. Indeed the uniqueness of its structure, as well as its pharmacokinetic behavior, led to discovery of FK228 as a prodrug. Based on these findings, potent derivatives of the metabolites mimicking the structures of FK228 have been synthesized.

Pharmacology Shortly after its isolation, FK228 was shown to reverse Ha-ras transformed cells and down-regulate c-myc expression. FK228 was also found to be highly toxic against various cancer cell lines during the In Vitro Cell Line Screening project at the National Cancer Institute, Development Therapeutics Program (NCI DTP). Later on, FK228 was found to be a potent histone deacetylase inhibitor. FK228 induces differential accumulation of acetylated histones, especially lysines at H3 and H subunits, promotes specific gene expression, restores cell differentiation and/or induces apoptosis at low nanomolecular concentrations.

FK228 can cause G1 and G2/M cell cycle arrest. The G1 arrest is by down-regulation of cyclin D1 and induction of p53-independent p21Waf1 and 12INK4A, which results in Retinoblastoma (Rb) hypophosphorylation. The mechanism of G2/M arrest is probably via formation of aberrant spindles by interfering with chromosome attachment, causing mitotic accumulation without affecting mitotic microtubules.

FK228 induces apoptosis in cancer cells by various mechanisms. Apoptosis via the TNF-receptor pathway (extrinsic) has been observed in non-proliferating CLL cells by down-regulation of FLICE-inhibitory protein (FLIP). FLIP acts downstream of Fas to inhibit TNF-receptor mediated apoptosis by binding to adaptor protein FADD and caspase 8, and thus interfering with caspase 8 activation. FK228 also causes apoptosis via the extrinsic pathway by induction of Fas ligand in various osteosarcoma cells. However, FK228-induced apoptosis also occus via the mitochondrial (intrinsic) pathways as evidenced by mitochondrial membrane damage after FK228 treatment. Therefore, it seems that the primary mechanism of FK228-induced apoptosis may vary among different cancer cells, and its IC50 ratios between normal blood mononuclear cells and peripheral CLL blast cells from patients with were between 20~50 (n=10).

FK228 inhibits hypoxia-stimulated tumor angiogenesis in vivo by suppression of various angiogenic growth factors. Hypoxia-inducible factor-1 (HIF-1) plays a pivotal role in cellular response (i.e. angiogenesis) to low oxygen concentrations. FK228 was found to inhibit HIF-1 expression in hypoxic tumors. Under hypoxia, induction of another important angiogenic growth factor, vascular endothelial growth factor (VEGF), can also be blocked by FK228 treatment. Moreover, FK228 inactivates the transcription of basic fibroblast growth factor (bFGF) in PC3 xenografts. Interestingly, FK228 exerts its angiostatic activity at low nanomolecular concentrations, which is of the same order of concentration required for its cytotoxicity. This suggests that FK228's antitumor activity is, at least in part, due to its anti-angiogenisis properties.

As an epigenetic modulator, FK228 is also a promising agent for gene therapy. FK228 enhances andeovirus transgenic expression in several malignant cell lines, as well as increases expression of the Na+/I− symporter and iodine accumulation in four poorly differentiated thyroid carcinoma cells lines.

Due to its promising activity, in vivo efficacy of FK228 has been extensively tested in mice bearing murine ascitic tumors, namely, P338 and L1210 leukemias, B16 melanoma, Colon 38 carcinoma, M5076 reticulum cell sarcoma, and Meth A fibrosarcoma, as well as human tumor xenographs including Lu-65 and LC-6 lung carcinomas, and SC-6 stomach adenocarcinoma. Significant tumor shrinkage was observed especially against murine Meth A fibrosarcoma and human SC-6 stomach adenocarcinoma. Moreover, FK228 is effective against P388 leukemias that are resistant to mitomycin C, cyclophosphamide, vincristine and 5-fluorouracil. The high antitumor activity and the lack of cross-resistance to other anticancer agents identify FK228 as a promising new drug. Several phase I trials were completed and show partial responses among patients with advanced or refractory cancers. Ongoing clinical trials of FK228 aim to investigate FK228 efficacy in patients with thyroid cancer, actue myeloid leukemia, Chronic Lymphocytic Leukemia, cutaneous T cell lymphoma, peripheral T cell lymphoma, follicular lymphoma, non-Hodgkin's lymphoma, anaplastic large cell lymphoma, mycosis fungoides and Sezary syndrome. A phase I trial was initiated in children with advanced cancers for toxicity evaluation. Moreover, clinical trials in combining FK228 with other therapeutic agents (i.e., Rituximab and Fludarabine) in treating patients with relapsed or refractory low-grade B-cell Non-Hodgkin's lymphoma were initiated.

Because the metabolites described herein are much more potent HDAC inhibitors than FK228, and much more potent anti-cancer agents than FK228, they are expected to be useful in treating the same cancers and conditions as FK228. These include P338 and L1210 leukemias, B16 melanoma, Colon 38 carcinoma, M5076 reticulum cell sarcoma, and Meth A fibrosarcoma, Lu-65 and LC-6 lung carcinomas, SC-6 stomach adenocarcinoma, murine Meth A fibrosarcoma, human SC-6 stomach adenocarcinoma, P388 leukemias that are resistant to mitomycin C, cyclophosphamide, vincristine and 5-fluorouracil. These agents are further expected to be useful in the treatment of other cancers, including but not limited to thyroid cancer, actue myeloid leukemia, Chronic Lymphocytic Leukemia, cutaneous T cell lymphoma, peripheral T cell lymphoma, follicular lymphoma, non-Hodgkin's lymphoma, anaplastic large cell lymphoma, mycosis fungoides and Sezary syndrome. Additionally, unlike FK228, these agents may be delivered specifically to target cells, thus making them more desirable agents for the treatment and prevention of diseases involving unwanted rapidly proliferating cells, such as cancers.

Preclinical pharmokinetics Preliminary FK228 rat pharmokinetic studies showed that FK228 follows a two-compartments model after i.v. bolus dosing with high total body clearance (425.3±117.7 mL/min. for 250 g rats) and large distribution volume (22.3±7.3 L/kg for 250 g rats). Oral bioavailability study in the rat showed that FK228 is poorly absorbed after oral dosing. Later on, FK228 was found to be a P-glycoprotein substrate (Pgp), suggesting Pgp may play a role in FK228 absorption and elimination. For example, Pgp-mediated efflux of FK228 back to intestinal lumen may result in poor intestinal absorption, and Pgp-mediated liver/renal excretion may be associated with the fast FK228 elimination. However, the role of Pgp in determining FK228 pharmokinetic behavior is yet to be studied. Interestingly, the total body clearance of FK228 from the rat is significantly higher than the rat cardiac output rate (74 mL/min. for a 250 g rat). This blood-flow independent clearance suggests an extensive mechanism of FK228 in the blood (and maybe the endothelial membrane of the blood vessels).

In order to find out the role of Pgp and RBC in FK228 disposition/elimination, and the effect of different dosing regimens on FK228 pharmacokinetics, we designed and conducted a series of pharmacokinetic studies in the rat. Results suggest that the glutathione (GSH) level in the RBC is a determinant of FK228 elimination in the rat. In vitro blood incubation studies subsequently demonstrated the formation of seven FK228 reduction and GSH conjugates, which were then identified by HPLC/multi-stage MS. Purification and in vitro HDAC inhibitors compared with the parent drug, suggesting that FK228 is a prodrug. This seems consistent with results from several other studies. For example, FK228's HDAC inhibitory effect is still observable after FK228 is quickly eliminated from circulation. Recently, it was found FK228, after reduction by dithiothreitol (DTT), showed a 40-fold increase in HDAC inhibitory activity. The structure of the active reduction product was found to be identical to one of the metabolites identified.

Clinical pharmacokinetics and toxicity In a phase I trial, FK228 was given to patients with a 4-hour infusion at doses beginning at mg/m$^2$, which represented one-third of the minimum toxic dose in dogs. The plasma concentration-time profile of FK228 was found to follow a two-compartment model and showed linear pharmacokinetics at doses between 1-24.9 mg/m$^2$. The maximum tolerated dose (MTD) was found to be 17.8 mg/m$^2$. However, due to large variations among patients, as well as a small patient number at each dose, the calculated pharmacokinetic parameters were not reliable. In order to gain a better characterization of FK228 pharmacokinetics and to seek potential clinical covariates that account for the inter-individual variations, we conducted a pharmacokinetic study in 20 AML and CLL patients receiving FK228 at 13 mg/m$^2$ given by a 4-hr i.v. infusion.

Transport and uptake Even though FK228 was found to be a Pgp substrate during the NCI screening, no kinetic information of FK228 transport in the presence or absence of Pgp inhibitors was available. In addition, there is no information available about whether FK228 also possesses affinity to other membrane transporters, or whether Pgp and other tranporters play a role in acquired FK228 resistance. We have studied FK228 transport and uptake kinetics using multiple cellular models. FK228 was a substrate for both Pgp and multidrug resistant-associated protein 1 (MRP1). By developing multiple FK228 resistant cell lines, we established for the first time that Pgp induction is the primary mechanism for the acquired resistance in cancer cells by histone hyperacetylation at the promoter region of Pgp.

Figure 2:
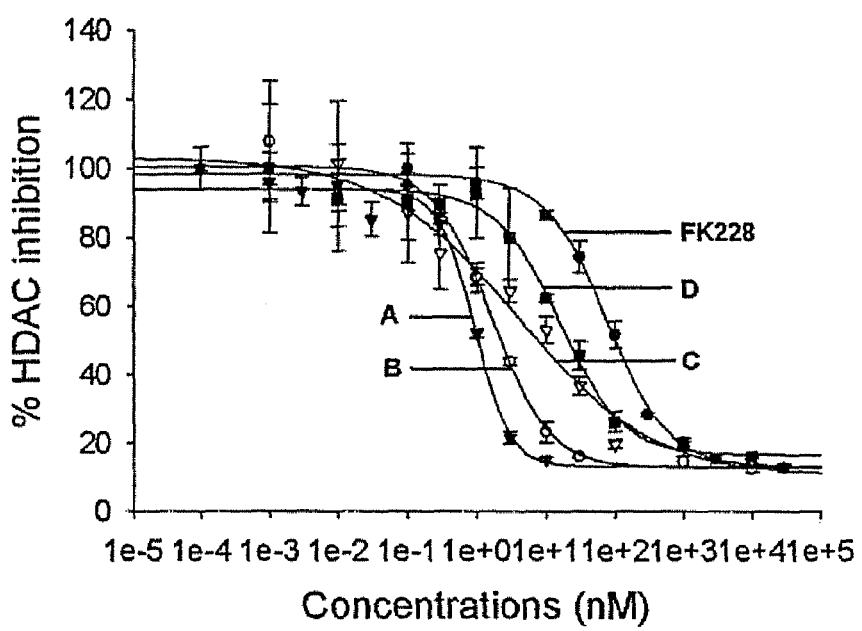
FIG. 2 shows dose-response curves of FK228 and metabolites A, B, C, and D. The HDAC inhibitory activity was determined using the Fluor de Lys HDAC Fluorescent Activity Assay/Drug Discovery Kit (n=3). The $IC_{50}$s were: FK228 76.5±5.9 nM, A 1.65±0.24 nM, B 0.94±0.14 nM, C 4.0±1.9 nM, and D 15.9±2.7 nM.

Pharmacological activity of FK228 metabolites As indicated below, a total of six metabolites were identified by MS$^n$ LC-MS techniques. Four most abundant FK228 metabolites, namely, A, B, C, and D were prepared in rat plasma and purified by HPLC. The purity of the metabolites was examined by MS and MS$^2$, followed by HDAC inhibition assay. The HDAC inhibition curves of FK228 and its metabolites A, B, and C are shown in FIG. 2. The $IC_{50}$s of FK228, A, B, C, and D were determined to be 76.5±5.9, 1.65±0.24, 0.94±0.14, 4.0±1.9 nM and 15.9±nM, respectively (n=3).

Formation and translocation of FK228 and its metabolites in rat blood incubation The fates of FK228 and its metabolites in rat plasma containing 10 mM GSH were followed by LC-MS. Due to a lack of the metabolite reference standards at the time we conducted this experiment, we could only determine the relative amounts of metabolites by normalizing their peak areas to that of FK228 at time 0. Upon mixing of FK228 at 100 μg/mL with rat plasma containing 10 mM GSH, FK228 concentrations decreased to about 30% within 2 min., and remained essentially constant thereafter. The two reduced thiol metabolites A and B reached their peak concentration rapidly, followed by approximately parallel decays with terminal half lives of 18.5 min. and 14.4 min., respectively. Concentrations of GSH conjugate C reached a plateau after 1 hr., followed by a two-phase decay. Conjugate D reached its maximum concentration at 1 hr., followed by a slow decline. Concentrations of conjugate E increased over time and reached its plateau at 2 hr. Due to the sensitivity limit, it was difficult to follow the profile of F.

Experimental Procedures

Materials Depsipeptide FK228 (purity ≧99%) was provided by the Drug Synthesis and Chemistry Branch, the National Cancer Institute (Bethesda, Md., USA). M-Ethylmaleimide (NEM), diethyl maleate (DEM), cyclosporin A (CsA) and N-t-Boc-Met-Leu-Phe (BMLP, purity ≧97%) were purchased from Sigma-Aldrich (St. Louis, Mo., USA). Potassium phthalate buffer (pH 4, 50 mM) was obtained from Can Water and Roger Scientific (Chicago, Ill. USA). The HPLC-grade water (≧18 mΩ) was generated from an E-pure water purification system (Barnstead, Dubuque, Iowa, USA). Acetonitrile (HPLC grade), acetic acid and ethyl acetate (reagent grade) were purchased from Fisher Scientific (Pittsburg, Pa., USA). Drug free heparinized rat and human plasma was purchased from Harlan Bioproducts for Science (Indianapolis, Ind., USA). Human albumin (Fraction V, 96~99%) was purchased from Sigma-Aldrich (St. Louis, Mo., USA).

Instrumentation LC-MS for quantification: The system consisted of a Shimadzu HPLC (Shimadzu, Columbia, Md.) and a Perkin-Elmer Sciez API 300 triple quadrupole mass spectrometer (PE Sciex, Thronhill, Ontario, Canada) equipped with an atmospheric pressure electrospray ionization source (ESI). For FK228 quantification, multiple reaction monitoring (MRM) was used and the monitored collision induced dissociation (CID) pathways for FK228 and the internal standard BMLP were at m/z 541.2/424 and 510/217, respectively, using instrument parameters as previously described (Chan et al., 1997; Li and Chan, 2000). For detection of FK228 metabolites, selected ion monitoring (SIM) was used, and the instrument parameters were tuned with FK228.

LC-MS for structural analysis: The system consisted of a Shimadzu HPLC system (Shimadzu, Columbia, Md.) and a LCQ ion-trap mass spectrometer (Finnigan MAT, San Jose, Calif.) couple to an ESI source. The positive ion mode was used and the general system parameters were tuned with FK228. The temperature of the heated capillary was set at 200° C. and the spray voltage was 5 kV. Full scan ranging from 100 to 1200 m/z, SIM and multiple stage MS (MS$^n$) scans of interest ions were conducted as needed. Collision energy levels (He) and activation times for the MS$^n$ analysis were adjusted for the compounds individually.

Pharmacokinetics and tissue distribution studies in the rat Twenty-three male S.D. rates weighing 250-300 g were divided into 5 groups. All rats were cannulated by the left jugular vein under ketamine anesthesia (im, 100 mg/kg) for drug administration and/or blood sampling. The rats were kept in metabolism cages and allowed to recover overnight with food and water given ad libitum. The animal protocols were approved by the Institutional Laboratory Animal Care and Use Committee (ILACUC) of the Ohio State University Laboratory Animal Resources (ULAR), and adhered to the guideline and "Principles of Laboratory Animal Care" by National Institutes of Health (NIH).

In the first group of 6 rats, FK228 dosing solution of 1 mg/mL, dissolved in 40% propylene glycol, 10% ethanol (USP) and 50% normal saline, was given by i.v. bolus to each rat as 2 mg/kg through the left jugular vein cannula followed by flushing the cannula with 2 volumes of normal saline. At the time schedule of predose, 5, 10, 20, 5, 60, 120, 180, 300 minutes after doing, blood samples of 0.2 mL each were withdrawn from the same cannula with an equal volume of normal saline. Plasma was separated immediately by centrifugation (10,000 g×0.5 min.) extracted with 10-volume ethyl acetate. After centrifugation, the organic layer was transferred into a clean conical Falcon polypropylene tube, and evaporated under a stream of nitrogen. The residue was dissolved in 100 μL 70% acetonitrile, and a 40 μL aliquot was used for FK228 determination. Weighed wet organ tissue samples were homogenized in appropriate volumes of blank human plasma with an Ultra-Turrax SDT1610 electric homogenizer (Tekmar, Cincinnati, Ohio) at the highest speed setting for 10 seconds 4 times. The reason for using human plasma was because FK228 is stable in human plasma and binds over 90% to plasma proteins, thus the addition of human plasma was expected to facilitate drug removal from organ tissues. The homogenates were then extracted and determined as in plasma samples (Chan, et al. 1997; Li and Chan, 2000). Feces samples were homogenized similarly as above. After centrifugation, the supernatant was extracted and determined as plasma samples.

A 2 mm×50 mm Keystone BetaBasic-C8 column (Keystone, Bellefonte, Pa.) and an isocratic elution were used with the mobile phase consisting of 70% acetonitrile and 0.1% acetic acid at a flow rate of 0.2 mL/min. The flow leaving the HPLC column was split in a ratio of 20:1, with only 10 μL/min. entering the mass spectrometer. All samples were determined by individual calibration curves using specific blank sample matrix. The FK228 dose recoveries from heart, lung, liver, kidney, brain, spleen, testes were calculated as FK228 amount=FK228 concentration in homogenate×homogenate volume. While the recoveries from rat muscle and fat samples were further normalized to whole body weight assuming the muscle and fat compose 40 and 4% of the rat total body weight, respectively (Davies and Morris, 1993).

Animal and human in vitro blood distribution studies Fresh whole blood obtained from male S.D. rats or human volunteers was heparinized (14 U/mL) and the hematocrit measured (Chen et al., 1992) The blood was spiked with FK228 (10×) to make final concentrations of 0.1, 1, and 10 μg/mL, and tehn incubated in a 37° C. water bath with agitation. Aliquots of 0.2 mL were removed at pre-selected time points of 2, 4, 6, 8, 10, 12, 16, 20, 30, 45, and 60 minutes. The samples were centrifuged and plasma was separated and kept frozen at −80° C. until analysis. Following the 1-hour incubation, 1 mL aliquot of blood was centrifuged and the RBC fraction was washed three times with 0.5 mL ice-cold drug-free rat plasma, 1 min. each time. The plasma washings were kept frozen at −80° C. until analysis. Since the uptake/removal of FK228 from plasma was rapid, the time-0 plasma samples were prepared by spiking FK228 stock solution into appropriate volumes of plasma corresponding to 1 mL blood, which was calculated according to: plasma volume of 1 mL blood=(1−H)+0.9×H, where H is the hematocrit value, and 0.09×H accounts for the residual plasma volume in the packed RBC (Chen et al., 1992).

The same procedure was repeated following pretreatment of rat blood with 10 mM NEM, a GSH depleting agent, at room temperature for 30 min. Saline pretreatment was used as the control. Plasma samples were extracted and FK228 concentrations were determined as described above. The % FK228 removed due to uptake/metabolism was calculated.

A FK228 study was conducted, wherein 2 mL fresh, heparinized rat whole blood containing 10 μg/mL FK228 was incubated at 37° C. for 1 hour. After centrifugation, the plasma was removed and the RBC fraction was washed 8 times with 2 mL saline each. Then drug-free rat plasma was added to the RBCs to restore original volume. The reconstituted blood was homogenized with a glass tissue grinder (400 strokes) followed by centrifugation at 16,000 g for 15 minutes, and 0.95 mL supernatant was removed. The RBC debris was further washed with 1 mL acetonitrile each 8 times. FK228 concentrations in plasma, saline washes, lysis supernatant, and acetonitrile washings were determined as described above and the cumulative recovery of FK228 was calculated. For the distribution study of FK228 and its metabolites, rat blood, after incubation with 10 μg/mL FK228 at 37° C. for 60 minutes, was centrifuged. The RBC fraction was homogenized, and FK228 concentrations in the plasma and cytostol were analyzed by LC-MS using SIM.

FK228 stability evaluation The stability of FK228 at μg/mL at 37° C. was evaluated in rat plasma alone, rat plasma containing 10 mM GSH, or rat plasma containing 10 mM GSH but pretreated with 10 mM NEM for 30 minutes. FK228 stability in RBC cytosol and normal saline was also studied. Aliquots of 0.2 mL were removed at pre-selected time points up to 1 hour and determined as before.

Formation kinetics, distribution, and HDAC inibitory activity assays of FK228's metabolites FK228 (100 μg/mL) was incubated in rat plasma containing 10 mM GSH at 37° C. Serial samples were removed at pre-selected time points up to hours. FK228 and its major metabolites were monitored by ESI LC_MS on the API instrument.

One mL rat blood containing 100 μg/mL FK228 was incubated at 37° C. for 60 minutes. The blood was centrifuged to remove plasma. To the RBC fraction was added blank rat plasma to restore the initial volume, and the mixture was homogenized by a glass tissue grinder (400 strokes). The plasma and RBC homogenates were analyzed by ESI ion-trap LC-MS. A Waters Spherisorb S3 ODS1 column (2 mm ID×10 cm, particle 5 μm, Waters Corporation, Milford, Mass., USA) with a gradient elution was used. The gradient was initiated with 25% acetonitrile in 0.1% acetic acid for 5 minutes, followed by a linear increase to 70% acetonitrile over 5 minutes, which was kept constant for 15 minutes. The mobile phase was then returned linearly to the original condition over 3 minutes, which was then maintained for 7 minutes. The cycle time for each analysis was 35 minutes.

One mL rat plasma containing 10 mM GSH and 100 µg/mL FK228 was incubated in a 37° C. water bath with agitation for 60 minutes. To the plasma was added 2 mL acetonitrile to precipitate the proteins. After centrifugation, the acetonitrile layer was transferred to a clean Falcon polypropylene tube and evaporated to dryness under a stream of nitrogen. The residue was reconstituted in 25% acetonitrile and analysed by ion-trap LC-MS. The metabolites were prepared as above from 10 mg FK228 and purified by HPLC. Their purities were further confirmed by ESI LC-MS. Their HDAC inhibitory activities were assayed by using the Fluor de Lys HDAC Fluorescent Activity Assay/Drug Discovery Kit (BioMol, Plymouth Meeting, Pa.).

Results

Rat pharmacokinetics Plasma concentration-time data from the rat were fitted to a two-compartment model using WinNonLin, and the computed relevant phannacokinetic parameters are listed in Table 1. As shown, the i.v. bolus group showed PK parameters similar to the previously published data (Chan et al., 1997; Li and Chan, 2000). FK228 showed a large distribution volume (32.7±4.51 L/kg) and a rapid total body clearance (237±58 mL/min). I.v. infusion led to a significant decrease in distribution volume (11.8±2.7 L/kg, $p<0.001$) and an increase in AUC (6194±881 nM·min, $p<0.002$), while an insignificant increase in $CL_{total}$ (178.6±27.5 mL/min, p=0.06) as compared with those of the i.v. bolus group. In the i.v. bolus groups, CsA pretreatment caused no significant changes in the pharmacokinetic parameters as compared to those of FK228 alone. DEM pretreatment resulted in a 50% depletion of RBC GSH and much higher $C_0$ (1185±637 nM, $p<0.05$) than those of FK228 alone. Other parameters (AUC, Vd and $CL_{total}$) did not show a significant change ($p>0.1$). The DEM treated group showed large variation in pharmacokinetic parameters, probably due to inconsistent in vivo GSH depletion.

FK228 concentrations declined rapidly, with over 20% remaining within 2 minutes in an apparent concentration-independent manner between concentration range 0.1-10 µg/mL. The RBCs were then separated y centrifugation and washed with ice-cold normal saline, followed by post-wash incubation in drug free rat plasma at 37° C. Only a small amount of drug was recovered in these fractions. Since FK228 is stable in rat plasma alone, this suggested that there was either an entrapment of metabolism of FK228 by rat RBC.

To further evaluate if the uptake/metabolism of FK228 is reversible, we determined the recoverable FK228 from the rat blood incubation system by HPLC-MS. The cumulative recovery of FK228 was <35%, suggesting significant metabolism.

The uptake of FK228 in human blood incubation system, however, showed apparent concentration dependence. FK228 was removed from plasma more rapidly and extensively at 10 µg/mL than at 1 µg/mL. Due to the relative structural simplicity of RBC membrane, this concentration-dependent uptake/metabolism suggests that FK228 may be a substrate of MRP1, which is involved in multidrug resistance and highly expressed on normal RBC membrane. To test if MRP1 does play a role, we treated human RBC with a specific MRP1 inhibitor MK571 (50 µM), the resulting RBC showed increased FK228 uptake/metabolism rate and extent of uptake at 0.1 µg/mL.

Involvement of GSH and plasma/cytosolic proteins in rat RBC uptake of FK228. Pretreatment with NEM (10 mM), an agent known to deplete intracellular GSH, not only significantly decreased the rate and extent of FK228 uptake/metabolism, but also increased the amount recoverable from RBC in the in vitro blood incubation. To investigate what factors were involved in the metabolism reactions, a series of stability tests were performed. FK228 was stable in rat plasma, saline, or saline containing 10 mM GSH at 37° C. for at least 4 hours. Only in the presence of plasma containing 10 mM GSH or RBC cytosol, was FK228 unstable over time. Again, this reaction was completely prevented after 10 mM NEM pretreatment. This suggests both GSH and plasma/cytosolic proteins are involved in the metabolism.

TABLE 1

| PK Parameters | I.v. bolus (n = 6) | I.v. infusion (n = 6) | I.v. bolus with CsA pretreatment (n = 3) | I.v. bolus with DEM pretreatment (n = 5) |
| --- | --- | --- | --- | --- |
| $AUC_\infty$ (nM · min) | 4097 ± 937 | 6194 ± 881 | 4004 ± 249 | 5419 ± 1450 |
| $C_{max}$ (nM) | 490 ± 164 | 25.3 ± 3.7 | 548 ± 249 | 1185 ± 637 |
| $Vd_{ss}$ (L/kg) | 32.7 ± 4.5 | 10.8 ± 2.7 | 29.0 ± 3.2 | 22.4 ± 13 |
| $Cl_{total}$ (mL/min) | 237 ± 58 | 178.6 ± 27.5 | 249 ± 18 | 276 ± 152 |
| MRT (min) | 36.3 ± 9.8 | 17.7 ± 3.2 | 27 ± 2.4 | 30 ± 16 |

The dose recovery from the 9 major organ tissues showed that liver is the organ with the highest FK228 recovery with 1.5±0.77% at 6 hours and 0.23±0.16% at 24 hours after dosing. Recovery from muscle also accounted for 0.87±0.51% at 6 hours and 0.31±0.18% at 24 hours after dosing. However, the total recoveries of the intact FK228 were low, only 2.5±1.26% and 0.56±0.3% at 6 hours and 24 hours, respectively. Dose recoveries from 24 hour urine, 24 hour pooled feces and intestinal contents, and 6 hour bile accounted for 5.9±1.6% (n=6), 0.23±0.079% (n=6) and 4.76±0.34% (n=3), respectively. The sum amounts of unchanged FK228 recovered from plasma, various major organs and tissues, urine and bile was less than 15% of the dose administered.

Figure 3:
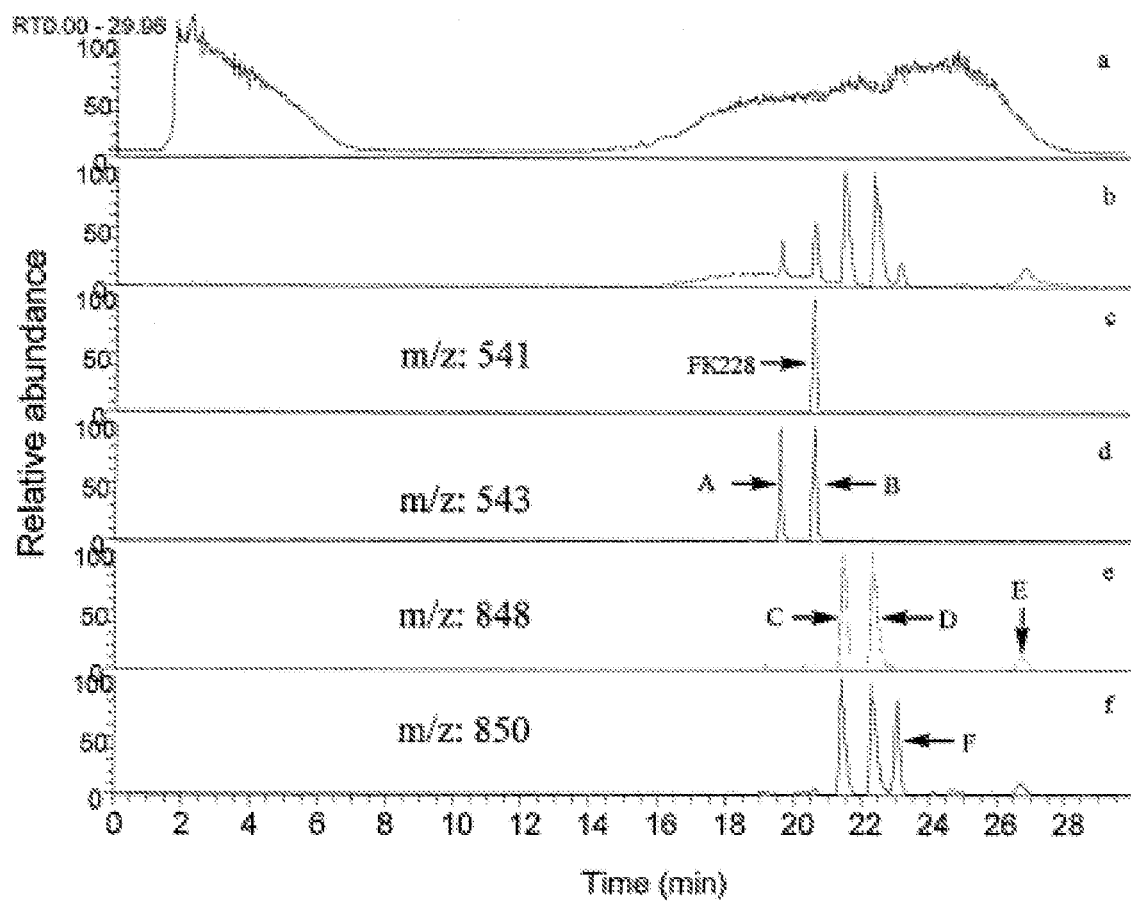
FIG. 3 HPLC/ESI-MS chromatograms of extracts from the in vitro incubation of rat plasma incubated with 100 μg/mL FK228 and 10 mM GSH. (a) Total ion chromatogram (TIC) of blank rat plasma extract; (b) TIC of the extract from the in vitro incubation; (c) extracted ion chromatogram (XIC) of FK228 at m/z 541; (d) XIC of two reduction products A and B at m/z 543; (e) XIC of three single GSH-FK228 conjugates C, D, and E at m/z 848; and (f) XIC of one reduced GSH-FK228 conjugate F at m/z850.

Uptake of FK228 by rat and human RBC Following the in vitro incubation of FK228 in rat blood at 37° C., plasma Determination of HDAC inhibitory activity of purified FK228 metabolites. The involvement of GSH suggested formation of FK228-GSH conjugate(s) and/or reduction product(s). Samples from incubation system containing rat plasma, 10 mM GSH, 10 µg/mL FK228 were separated by HPLC gradient elution and analyzed by full scan LC-MS (FIG. 3). A total of 6 metabolites, shown in FIG. 1, were identified by MS" LC-MS techniques as previously published (Xiao et al., "Identification of thiols and glutathione conjugates of depsipeptide FK228 blood." *Rapid Commun Mass Spectrom* 17: 757-766, 2003, incorporated herein by reference).

Four most abundant FK228 metabolites, namely A, B, C and D were prepared in rat plasma and purified by HPLC. The purity of metabolites was examined by MS and $MS^2$, followed by HDAC inhibition assay. The HDAC inhibition curves of FK228 and its metabolites A, B and C are shown in FIG. 2. The $IC_{50}$s of FK228, A, B, C and D were determined to be 76.5±5.9, 1.65±0.24, 0.94±0.14, 4.0±1.9 nM and 15.9±2.7 nM, respectively (n=3).

Formation and translocation of FK228 and its metabolites in rat blood incubation. The fates of FK228 and its metabolites in rat plasma containing 10 mM GSH were followed by LC-MS. Due to a lack of the metabolite reference standards at the time the experiment was conducted, only the relative amounts of metabolites could be determined; this was done by normalizing their peak areas to that of FK228 at time 0. Upon mixing of FK228 at 100 μg/mL with rat plasma containing 10 mM GSH, FK228 concentrations decreased to about 30% within 2 minutes, and remained essentially constant thereafter. The two reduced thiol metabolites A and B reached their peak concentrations rapidly, followed by approximately parallel decays with terminal half lives of 18.5 minutes and 14.4 minutes, respectively. Concentrations of GSH conjugate C reached a plateau after 1 hour, followed by a two-way phase decay. Conjugate D reached its maximum concentration at 1 hour followed by a slow decline. Concentrations of conjugate E increased over time and reached its plateau at 2 hours. Due to the sensitivity limit, it was difficult to follow the profile of F.

Figure 4:
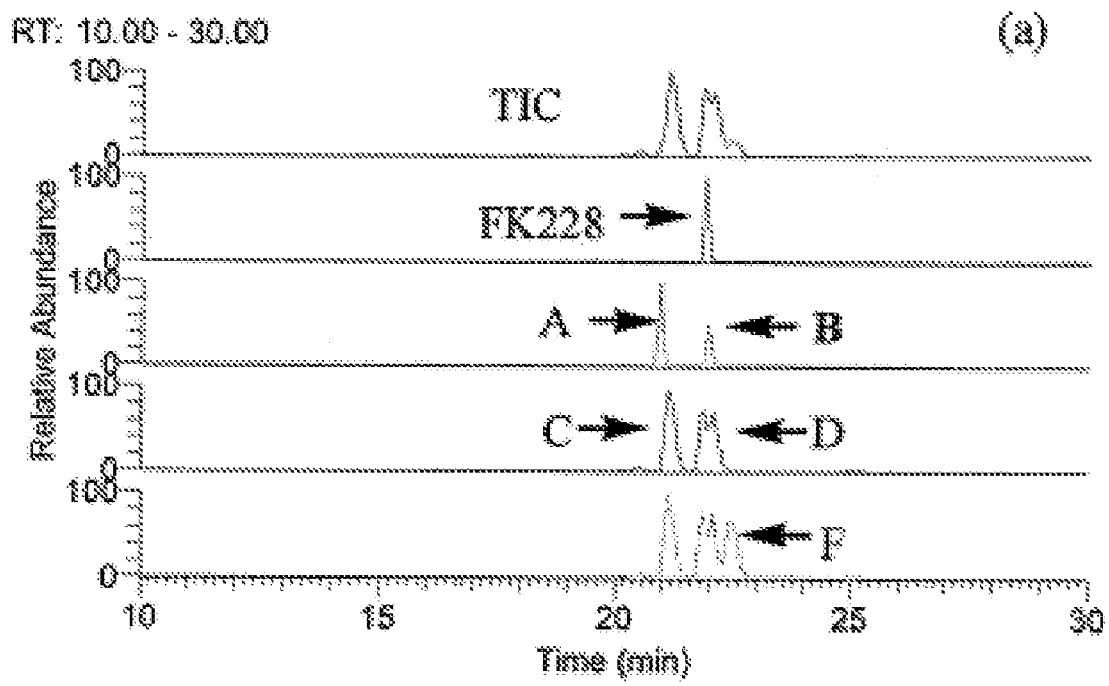
FIG. 4 shows the fates of FK228 metabolites after their formations in rat RBC. After FK228 (100 μg/mL) was incubated in rat whole blood at 37° C. for 60 min., FK228, metabolites A, B, C, D and F were detected in the plasma fraction (a); while FK228, metabolites B, D and E were detected in the RBC homogenate (b).
Figure 4:
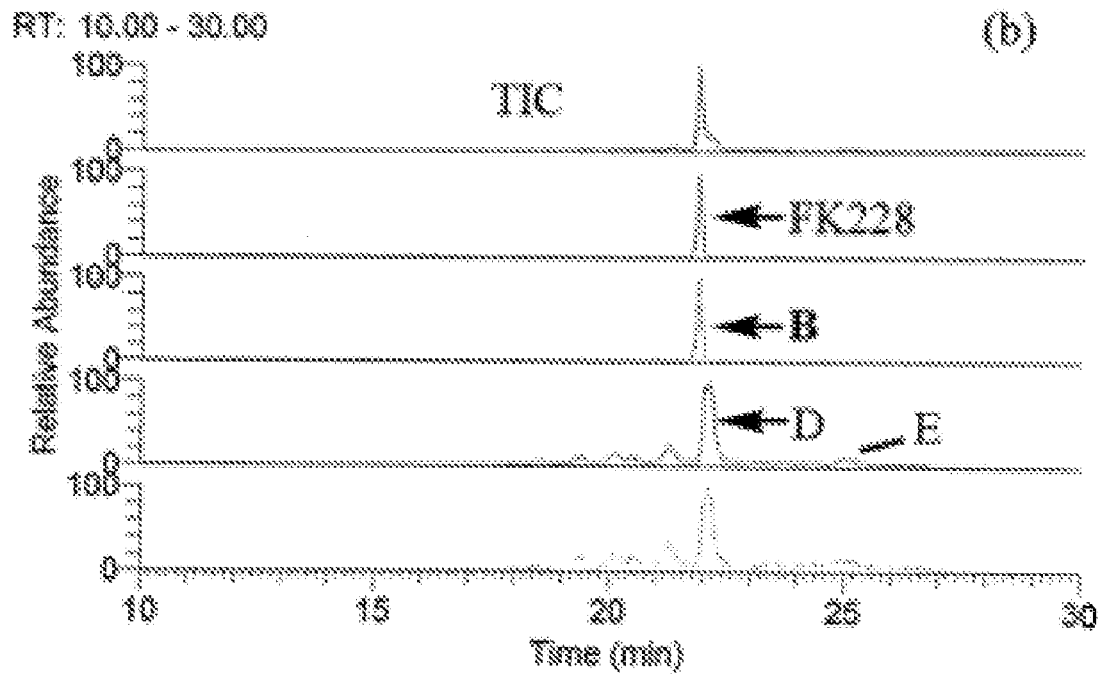

Following a 1 hour incubation at 100 μg/mL FK228 in fresh heparinized rat whole blood at 37° C., FK228 and its metabolites A, B, C, D and F were detected in plasma. In RBC cytosol, only FK228 and its metabolites B and D were detected. In both fractions, metabolite E was found to be a minor peak as shown in FIG. 4.

Rat pharmocokinetics and mass balance of FK228. Although FK228 pharmacokinetics has been studied in the rat and human, little is known about its mechanisms of disposition and elimination. The current pharmacokinetic results in the rat confirm a large $CL_{total}$, higher than the rat cardiac output (74 mL/min). This phenomenon may suggest extensice FK228 metabolism in the blood, which could lead to apparent blood-flow-independent drug eliminations.

FK228 was detected in rat urine and bile. FK228 has been reported to be a substrate of Pgp which is highly expressed in the rat kidneys and liver. Thus Pgp is likely to be involved in FK228 renal and biliary eliminations. However, the total amount of FK228 in 24-hour urine and 6-hour bile only accounted for less than 11% of the dose, and no apparent major metabolite was found in urine and bile by HPLC/MS analysis, suggesting existence of other major elimination pathway(s). The amount of FK228 in feces was much lower than excreted in bile, only 0.23%, suggesting possible degradation in intestinal contents, since FK228 is known to be poorly absorbed in intestine. The low overall FK228 recovery as the intact drug (15%) suggested extensive metabolism in blood.

CsA pretreatment resulted in little change of the FK228 plasma concentration-time profile. This suggests Pgp is not a major factor in FK228 distribution and elimination, as supported by the low renal and liver excretions. A clinical trial of FK228 in combination with Pgp inhibitor(s) is about to be initiated at the National Cancer Institute. One prerequisite requirement for such combination is that the drugs' pharmacokinetic profiles should not be dramatically changed by the Pgp inhibitor, so as to avoid abnormal increases in blood concentrations and associates toxicities. Our data suggests the combination may be safe from the pharmacokinetic aspect of drug-drug interaction.

Iv. infusion in the rat showed a significant decrease in Vdss when compared to that following i.v. bolus at the same dose. This could be due to the existence of a saturable efflux transporter in tissues, which effluxes FK228 back to plasma effectively at low FK228 plasma concentrations, but becomes saturated at high FK228 concentration. Following i.v. infusion, the plasma FK228 concentrations were low (<20 nM), which led to effective efflux and trapping of FK228 in the plasma pool. This hypothesis is consistent with out in vitro human blood uptake/metabolism studies.

DEM pretreatment significantly decreased RBC intracellular GSH levels, and resulted in a higher $C_0$. This confirms GSH is involved in FK228 elimination and suggests that the RBC GSH level may serve as a determinant in FK228 clinical pharmacokinetics.

The role of RBC in FK228 disposition More attention has recently been drawn to the roles of RBC in modulating drug PK behaviors. For most drugs, the partition between RBC and plasma is approximately equal and reversible. In these cases, depending on the partition rate, RBC may modulate drug distribution volume, or delay drug elimination by trapping the drug in RBCs when blood flows through eliminating organs (e.g., liver). In some other cases, however, the drug uptake by RBC seems irreversible by either tight non-covalent binding or chemical modification. In our case, rat RBC uptake/metabolism FK228 is rapid and irreversible. Plasma/cytosolic proteins and GSH are involved in the formation of the six metabolites.

Human RBC, on the other hand, showed FK228 concentration-and hematocrit-dependent uptake/metabolism of FK228. MRP1 is thought to be highly expressed on RBC membrane. Recent data from a series of in vitro transport studies in our laboratory indicated that FK228 is a MRP1 substrate. Taken together, this concentration-dependent FK228 removal strongly suggests that human RBC MRP1 effectively effluxes FK228 at low concentration levels, but becomes saturated at higher concentrations. This efflux was further confirmed by MRP1 inhibition study, where specific MRP1 inhibitor MK571 reversed the efflux at low FK228 plasma concentration of 1 μg/mL and resulted in more rapid and extensive FK228 removal from plasma.

It is known that rat and human RBC contain similar concentrations of GSH (up to 10 mM), but in rat RBC cytosol, there are even higher concentrations of more reactive thiol-containing proteins. After FK228 molecule diffuses across RBC membrane, it is either pumped back to plasma by MRP1 or reacts with GSH or free thiols on cytosol proteins. In rat RBCs, it is even more likely for FK228 molecules to react with thiols or GSH, and thereby trapped inside RBCs, and form appartent conjugates and metabolites than in the human RBC. And as a result, rat RBC uptake/metabolizes FK228 more completely and rapidly than human RBCs. Even though no FK228 concentration-dependent uptake was observed in rat blood at the chosen FK228 concentrations, it is expected that at certain low FK228 concentration levels, MRP1-mediated efflux should be apparent. This is consistent with the rat i.v. infusion PK study, which showed decreased distribution volume, suggesting FK228 distribution, into tissues may be limited at concentrations below 20 nM.

Metabolism of FK228 We have identified 6 potential metabolites of FK228, identified as A, B, C, D, E and F and shown in FIG. 1, four of which, A, B, C, and F possess a free thiol group on the longer aliphatic chain. The thiol meets the structural requirements for reversible HDAC inhibitors. Computer docking simulation and chemical synthesis further confirmed the strong binding affinity of the thiol metabolite towards the class I HDAC active binding site. The free thiol group on the long aliphatic tail was shown to be important for HDAC binding.

The stabilities of the metabolites A through E were consistent with their proposed structures. The free thiol groups on A, B, and C render them instable, resulting in rapid decays. E is the GSH conjugation product on the α double bond to the carbonyl group. From a chemical point of view, the formation rate of E should be slow, but the product should be stable. Consistent with this, E showed a steady increase in concentration, although the overall abundance of E was not high.

An earlier in vitro study determined the active thiol A's HDAC inhibitory activity by testing transcription induction in P21 gene. However, since FK228 and its metabolites may have different transport and uptake behaviors, their intrinsic activity could not be compared by this method. Also, because A is unstable, it was of interest to find out if the other metabolites were also active. We performed Metabolites' purifications by HPLC/MS and activity evaluations by the fluorescent HDAC activity kit. The results showed that metabolites A, B, and C are at least 46, 82, and 19 times more potent as HDAC inhibitors than FK228, respectively. However, FK228 also showed quite low $IC_{50}$ of 76.5±5.9 nM. This was unexpected because according to the docking simulation, FK228 should not bind to the enzyme with high affinity. A reason for this may be that the HDAC assay kit contains high GSH or GSH-like activity, which activates FK228 during the HDAC inhibition assay. This was confirmed by a GSH activity assay using the Bioxytech GSH-400 assay kit, which showed a GSH-like activity equivalent to at least 24 mM GSH in the HeLa extract, which is a major component of the kit.

FK228 is more lipophilic than its metabolites and may diffuse passively into target cells, where it is biochemically activated. However, if RBCs play a major role in FK228 elimination, as suggested by our data, FK228 does not seem to be a good prodrug since it is not delivered specifically to its target cancer cells.

Because of the identities of GSH conjugates of the FK228 metabolites, and the relative simple cell membrane structure of RBC, it is reasonable to expect that FK228 and some of its GSH conjugates are MRP1 substrates. This was supported by our findings where metabolites A, C and F were pumped out of rat RBC, while only B and D remained in rat RBC after 1 hour whole blood incubation at 37° C. as shown in FIG. 4.

The examples described herein are for illustration and are not meant to limit the scope of the invention.

The invention claimed is:

1. A method of treating cancer in a subject in need of such treatment, wherein said cancer is susceptible to treatment with a histone deacetylase inhibitor, comprising administering a therapeutically effective amount of one or more metabolites of FK228, wherein said metabolites are selected from the group consisting of compounds B, C, D, E, F:

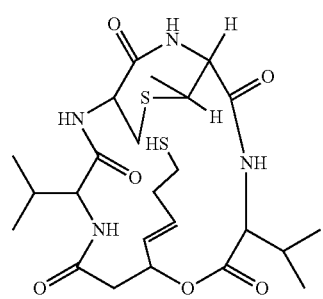

B

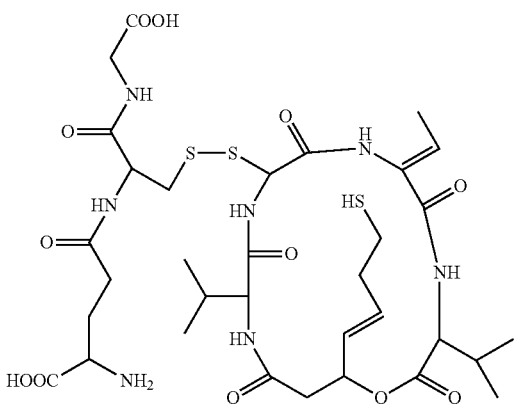

C

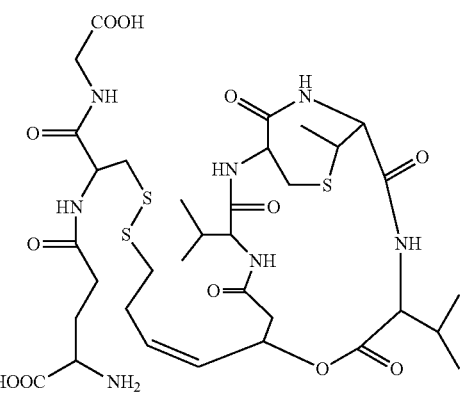

D

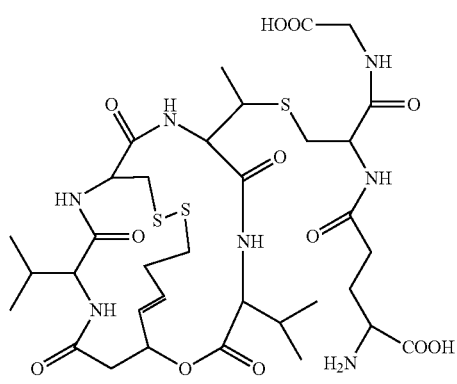

E

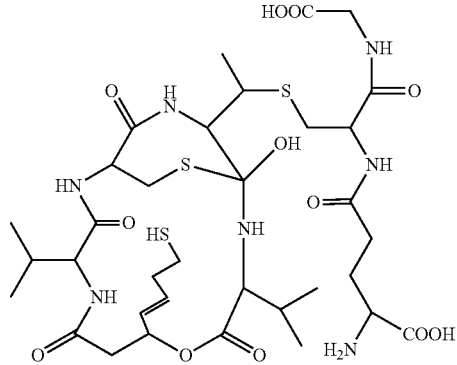

F and combinations thereof; and salts thereof.

2. The method of claim 1 wherein the metabolite is compound B or a salt thereof.

3. The method of claim 1 wherein the metabolite is compound C or a salt thereof.

4. The method of claim 1 wherein the metabolite is compound D or a salt thereof.

5. The method of claim 1 wherein the metabolite is compound E or a salt thereof.

6. The method of claim 1 wherein the metabolite is compound F or a salt thereof.

7. The method of claim 1 wherein the cancer is selected from the group consisting of P338 leukemia, L1210 leukemia, B16 melanoma, Colon 38 carcinoma, M5076 reticulum cell sarcoma, Meth A fibrosarcoma, Lu-65 lung carcinomas, LC-6 lung carcinomas, SC-6 stomach adenocarcinoma, murine Meth A fribrosarcoma, human SC-6 stomach adenocarcinoma, thyroid cancer, acute myeloid leukemia, Chronic Lymphocytic Leukemia, cutaneous T cell lymphoma, peripheral T cell lymphoma, follicular lymphoma, non-Hodgkin's lymphoma, anaplastic large cell lymphoma, mycosis fungoides and Sezary syndrome.

8. A method of inducing apoptosis in cancer cells susceptible to treatment with a histone deacetylase inhibitor, comprising contacting the cancer cells with a therapeutically effective amount of one or more metabolites of FK228, wherein said metabolites are selected from the group consisting of compounds B, C, D, E, and F:

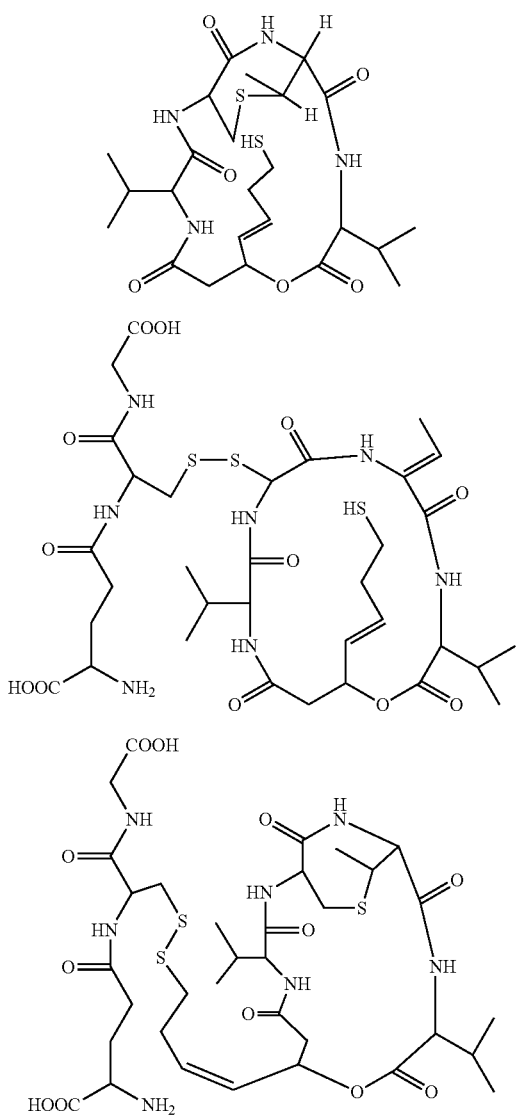

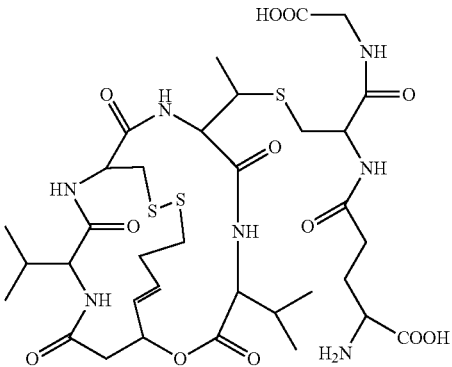

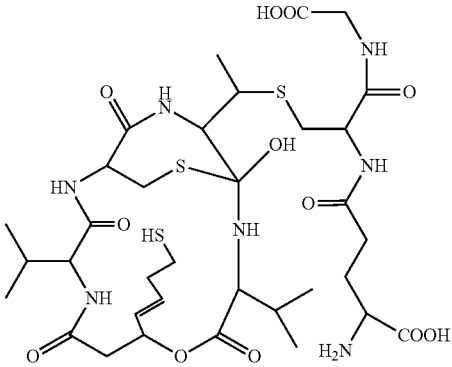

and combinations thereof; and salts thereof.

9. The method of claim 8 wherein the metabolite is compound B or a salt thereof.

10. The method of claim 8 wherein the metabolite is compound C or a salt thereof.

11. The method of claim 8 wherein the metabolite is compound D or a salt thereof.

12. The method of claim 8 wherein the metabolite is compound E or a salt thereof.

13. The method of claim 8 wherein the metabolite is compound F or a salt thereof.

14. The method of claim 8 wherein the cancer cells are selected from the group consisting of P338 leukemia cells, L1210 leukemia cells, B16 melanoma cells, Colon 38 carcinoma cells, M5076 reticulum cell sarcoma cells, Meth A fibrosarcoma cells, Lu-65 lung carcinoma cells, LC-6 lung carcinoma cells, SC-6 stomach adenocarcinoma cells, murine Meth A fribrosarcoma cells, human SC-6 stomach adenocarcinoma cells, thyroid cancer cells, acute myeloid leukemia cells, Chronic Lymphocytic Leukemia cells, cutaneous T cell lymphoma cells, peripheral T cell lymphoma cells, follicular lymphoma cells, non-Hodgkin's lymphoma cells, anaplastic large cell lymphoma cells, mycosis fungoides cells and Sezary syndrome cells.

15. The method of claim 1 wherein the metabolites are compounds B and D or salts thereof.

16. The method of claim 1 wherein the metabolites are compounds C and F or salts thereof.

17. The method of claim 15, wherein the cancer is selected from the group consisting of P338 leukemia, L1210 leukemia, acute myeloid leukemia, and Chronic Lymphocytic Leukemia.

18. The method of claim 16, wherein the cancer is selected from the group consisting of P338 leukemia, L1210 leukemia, acute myeloid leukemia, and Chronic Lymphocytic Leukemia.

19. The method of claim 15, wherein the cancer is selected from the group consisting of cutaneous T cell lymphoma, peripheral T cell lymphoma, follicular lymphoma, non-Hodgkin's lymphoma, anaplastic large cell lymphoma, mycosis fungoides, and Sezary syndrome.

20. The method of claim 16, wherein the cancer is selected from the group consisting of cutaneous T cell lymphoma, peripheral T cell lymphoma, follicular lymphoma, non-Hodgkin's lymphoma, anaplastic large cell lymphoma, mycosis fungoides, and Sezary syndrome.

21. The method of claim 8 wherein the metabolites are compounds B and D or salts thereof.

22. The method of claim 8 wherein the metabolites are compounds C and F or salts thereof.

23. The method of claim 21, wherein the cancer cells are selected from the group consisting of P338 leukemia cells, L1210 leukemia cells, acute myeloid leukemia cells, and Chronic Lymphocytic Leukemia cells.

24. The method of claim 22, wherein the cancer cells are selected from the group consisting of P338 leukemia cells, L1210 leukemia cells, acute myeloid leukemia cells, and Chronic Lymphocytic Leukemia cells.

25. The method of claim 21, wherein the cancer cells are selected from the group consisting of cutaneous T cell lymphoma cells, peripheral T cell lymphoma cells, follicular lymphoma cells, non-Hodgkin's lymphoma cells, anaplastic large cell lymphoma cells, mycosis fungoides cells, and Sezary syndrome cells.

26. The method of claim 22, wherein the cancer cells are selected from the group consisting of cutaneous T cell lymphoma cells, peripheral T cell lymphoma cells, follicular lymphoma cells, non-Hodgkin's lymphoma cells, anaplastic large cell lymphoma cells, mycosis fungoides cells, and Sezary syndrome cells.

* * * * *